United States Patent
Knowles et al.

(10) Patent No.: US 6,287,847 B1
(45) Date of Patent: Sep. 11, 2001

(54) BIODEGRADATION OF METAL CYANIDES

(75) Inventors: Christopher John Knowles, Woodstock; Vanessa Tett, Canterbury; Michelle Barclay, Oxford, all of (GB)

(73) Assignee: BG plc, Reading (GB)

( * ) Notice: Subject to any disclaimer, the term of this patent is extended or adjusted under 35 U.S.C. 154(b) by 0 days.

(21) Appl. No.: 09/147,386

(22) PCT Filed: Jun. 12, 1997

(86) PCT No.: PCT/GB97/01585
§ 371 Date: Aug. 23, 1999
§ 102(e) Date: Aug. 23, 1999

(87) PCT Pub. No.: WO97/47363
PCT Pub. Date: Dec. 18, 1997

(30) Foreign Application Priority Data

Jun. 14, 1996 (GB) .................................... 9612442

(51) Int. Cl.⁷ ....................................... B09B 3/00
(52) U.S. Cl. ............... 435/262.5; 435/262; 435/254.1; 435/256.3; 435/256.5; 435/256.7; 435/929; 435/933; 435/945
(58) Field of Search ................ 435/262, 262.5, 435/256.3, 256.5, 256.7, 254.1, 929, 933, 945

(56) References Cited

U.S. PATENT DOCUMENTS 4,894,341 * 1/1990 Richardson .................... 435/227

FOREIGN PATENT DOCUMENTS

| 0 061 249 | 9/1982 | (EP) . |
| 0 233 719 | 8/1987 | (EP) . |
| 0 234 760 | 9/1987 | (EP) . |
| 349 348 * | 1/1999 | (EP) . |
| 2 314 078 | 12/1997 | (GB) . |
| 895930 * | 1/1981 | (RU) . |
| 82-94781E/44 | 1/1981 | (WO) . |
| 86-067962/10 | 8/1985 | (WO) . |

OTHER PUBLICATIONS

Pereira et al. Isolation, selection and characterization of cyanide–degrading fungus from an industrial effluent. International Biodeterioration and Biodegradatin. 1996, vol. 36, No. 1–2, pp. 45–52.*

* cited by examiner

Primary Examiner—Sandra E. Saucier
Assistant Examiner—Vera Afremova
(74) Attorney, Agent, or Firm—Oblon, Spivak, McClelland, Maier & Neustadt, P.C.

(57) ABSTRACT

An iron cyanide complex is biodegraded by growing a fungus selected from *Fusarium solani, Trichoderma polysporum, Penicillium miczynski, Fusarium oxysporum,* and *Scytalidium thermophilum* in a medium containing the iron cyanide complex.

5 Claims, 2 Drawing Sheets

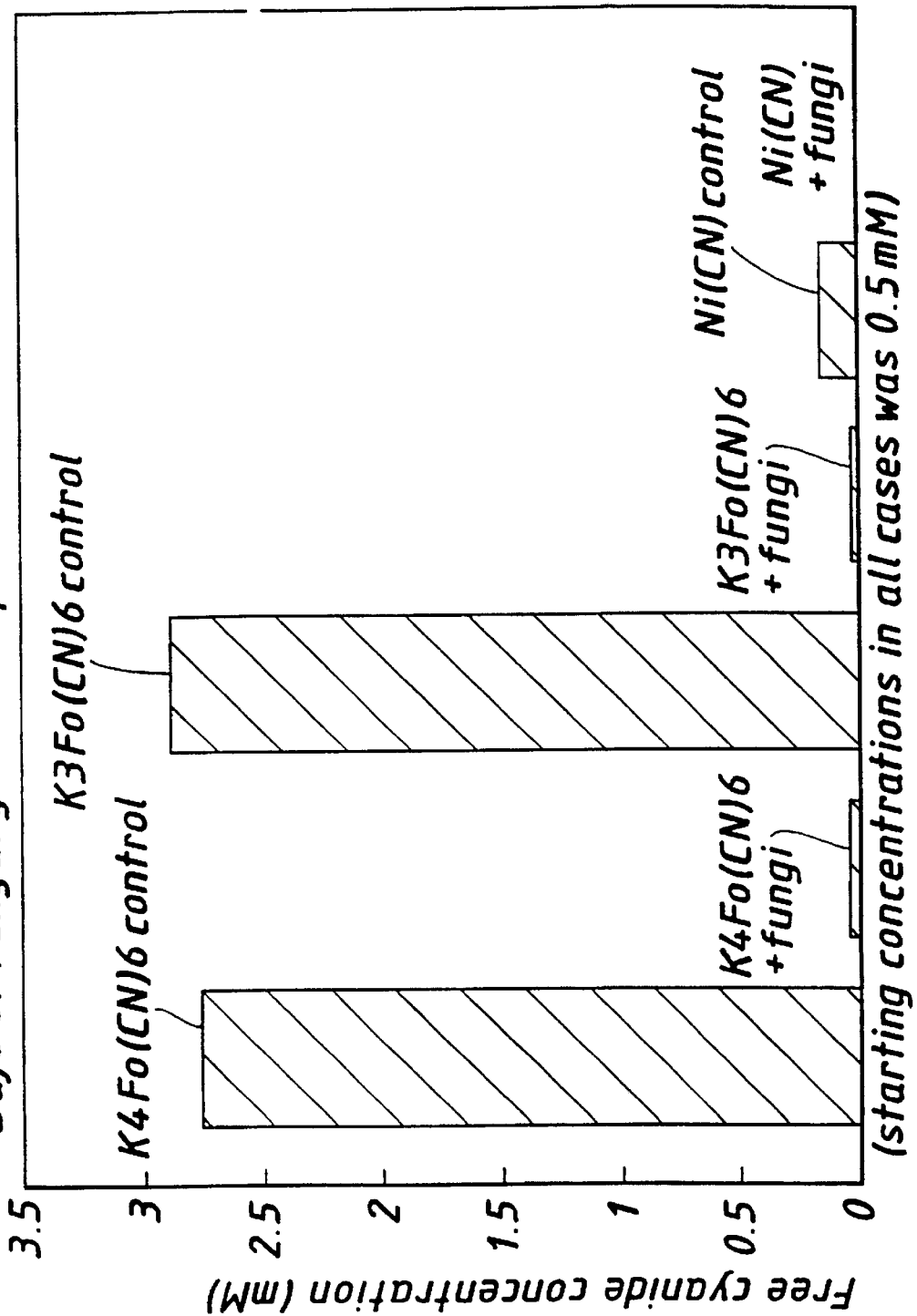

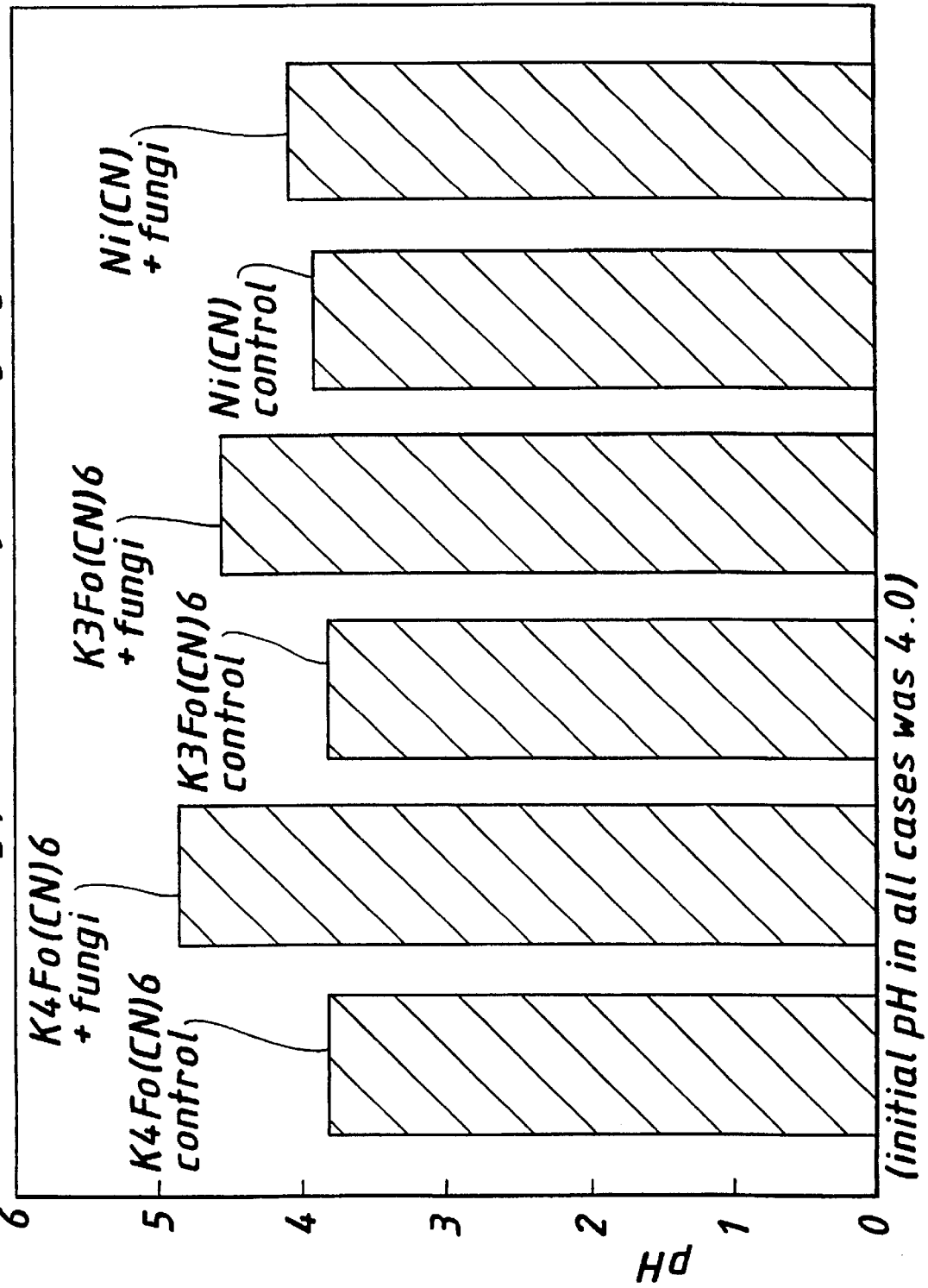
FIG. 2. Bar chart showing pH after 26 days of fungal growth. (initial pH in all cases was 4.0)

BIODEGRADATION OF METAL CYANIDES

BACKGROUND OF THE INVENTION

1. Field of the Invention

The present invention relates to the biodegradation of a metal cyanide or a mixture of two or more metal cyanides and particularly an iron cyanide or mixture of iron cyanides.

2. Discussion of the Background

Coal gasification to produce methane gas was common practice across most of Europe, the UK and USA throughout the nineteenth century to the mid 1960s. This process has fallen into general disuse leaving an estimated 5,000 former gasworks contaminated with the by-products of gasification and its subsequent purification These contaminants typically include inorganics such as sulphur and cyanide containing compounds, metals, volatile aromatics, phenolics and poly aromatic hydrocarbons (PAHs). The removal of hydrogen cyanide and hydrogen sulphide, by passing the gas through oxide purifiers containing iron oxide, resulted in the production of spent oxide containing up to 45,000 mg $Kg^{-1}$ of cyanide. Most of the cyanide is complexed with iron in the form of compounds such as Prussian Blue ($Fe_4[Fe(CN)_6]_3$), giving the spent oxide its characteristic blue colour. The solubility of Prussian Blue is strongly dependent on pH. Although highly stable and insoluble at low pH (typical of gasworks soil), above pH 4 the iron cyanide concentrations in groundwater, due to leaching and run-off, may exceed the Dutch maximum tolerated level of 200 $\mu g\ L^{-1}$ (equivalent to $1.28 \times 10^{-6}$ mM) (Meeussen et al, 1992). With this consideration Meeussen et al (1992) have determined that all Prussian Blue should be removed before iron cyanide concentrations will fall to a tolerable level. Biological processes where toxic compounds undergo complete mineralisation are often cheaper, and deemed more environmentally aware than chemical processes to remove such toxic chemicals. Isolation of an organism that has the ability to degrade iron cyanide compounds including Prussian Blue is therefore highly desirable.

Stemphylium loti is a pathogenic fungus of the cyanogenic plant birdsfoot trefoil. The fungus has been shown to induce cyan

$$H_2O + HCN \rightarrow HCONH_2$$

Fry and Millar (1972) also showed that the enzyme has an optimum pH activity range of 7.0 to 9.0.

Cyanide hydratase has since been purified from a number of other fungi including Fusarium laterium (Cluness et al, 1993) and Gloeocercospora sorghi (Wang and Van Etten, 1992).

The bacterium Pseudomonas Fluorescens NCIMB 11764, first isolated by Harris and Knowles (1983a), utilises KCN under nitrogen limiting conditions at neutral conditions in fed batch. The key enzyme in this case is cyanide oxygenase (Harris and Knowles, 1983b), where the cyanide is converted to ammonia which is subsequently utilised in industrial processes.

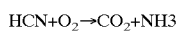

$$HCN + O_2 \rightarrow CO_2 + NH_3$$

Kunz et al (1992) later showed that cyanide hydratase is also present in a Pseudomonas species, although its activity is limited to higher concentrations of 20–50 mM cyanide.

A number of bacteria including Pseudomonas Fluorescens NCIMB 11764 (Rollinson et al, 1987), Pseudomonas putida BCN3 (Silva-Avalos et al, 199x) and Pseudomonas paucimobilis mudlock ATCC 39204 (see U.S. Pat. No: 4,461,834 to Mudder and Whitlock), have the ability to utilise moderately strong metal complexed cyanides in the form of nickel cyanide $[Ni(CN)_4^{2-}]$ in nitrogen limited batch or continuous culture at neutral pH values. Again cyanides oxygenase activity was observed.

Despite the fact that a number of metallo cyanides, including $Ni(CN)_4^{2-}$ and $Cu(CN)_4^{2-}$, have been shown to be biodegradable at neutral pHs (around pH7) by bacteria, no preculture of a micro-organism or a mixed culture of micro-organisms has been isolated with the ability to grow on iron cyanides. There is also no documentation of an organism capable of degrading metallo cyanides at a pH below about pH7. Likewise, although a number of fungi have been shown to tolerate cyanide, in the form of HCN, by detoxification using cyanide hydratase, a fungus has never been shown to grow on any metallo cyanide complex at pH7 or otherwise.

SUMMARY OF THE INVENTION

According to one aspect of the present invention, there is a provided a method for biodegrading a metal cyanide or a mixture of two or more metal cyanides comprising causing an organism to grow in a medium containing the cyanide or cyanides with the pH of the medium being 6 or less. Preferably the organism is a fungus.

According to another aspect of the present invention, there is provided a method for biodegrading a metal cyanide or mixture of two or more metal cyanides comprising causing a fungus to grow in a medium containing the cyanide or cyanides with the pH of the medium being 7.5 or less.

According to a further aspect of the present invention, there is provided a method for biodegrading an iron cyanide or mixture of two or more iron cyanides comprising causing a fungus to grow in a medium containing the cyanide or mixture of cyanides.

Preferably the pH of the medium is less than 7.5 and suitably lies between 3 and 6.

According to a still further aspect of the present invention the fungus is Fusarium solani (IMI 369371, which has been deposited in CABI Bioscience under the terms of the Budapest Treaty under the Accession number 380003 on Jan. 6, 1999).

According to a yet still further aspect of the present invention the fungus is Trichoderma polysporum (IMI 369372, which has been deposited in CABI Bioscience under the terms of the Budapest Treaty under the Accession number 380004 on Jan. 6, 1999).

According to a further different aspect of the present invention the fungus is Penicillium miczynski (IMI 370461, which has been deposited in CABI Bioscience under the terms of the Budapest Treaty under the Accession number 380005 on Jan. 6, 1999).

According to a different aspect of the present invention the fungus is Fusarium oxysporum (IMI 370462, which has been deposited in CABI Bioscience under the terms of the Budapest Treaty under the Accession number 380006 on Jan. 6, 1999).

According to a still further different aspect of the present invention the fungus is Scytalidium thermophilum (IMI 370463, which has been deposited in CABI Bioscience under the terms of the Budapest Treaty under the Accession number 380007 on Jan. 5, 1999).

CABI Bioscience is the successor to the International Mycological Institute (IMI). CABI Bioscience is located at Bakeham Lane, Egham, Surrey TW20 9TY, United Kingdom.

BRIEF DESCRIPTION OF THE DRAWINGS

The preferred embodiments of the invention will be describe in detail, with reference to the following figures, wherein:

FIG. 1 is a bar chart showing free cyanide concentration after 26 days of fungal growth at pH 4; and FIG. 2 is a bar chart showing pH after 26 days of fungal growth.

DETAILED DESCRIPTION OF PREFERRED EMBODIMENTS

Embodiments of the invention will now be particularly described with reference to the following:

Enrichments set up at pH4 (50 mM succinate/10 mM NaOH) using soil taken from a disused gasworks site yielded a mixed culture, including a fungus which has the ability to grow on metallo cyanide complexes including nickel cyanide (Ni $(CN)_4^{21}$), potassium ferricyanide ($K_4Fe(CN)_6$), potassium ferrocyanide ($K_3Fe(CN)_6$), and Prussian Blue ($Fe_4[Fe(CN)_6]_3$), when added as the sole source of nitrogen, and under acidic conditions (about pH4).

Growth was visible by the formation of a black fungal biomass. Growth did not occur when no nitrogen source was added to the medium. Removal of the iron cyanide complex was monitored by two methods. Firstly in the case of the iron cyanides, the blue coloration of the medium (due to the formation of the Prussian Blue) was depleted as the fungus grew until the medium became colourless. The control medium, which was not inoculated, remained blue. Secondly, by the metallo cyanide concentration in the medium, which was measured in terms of free cyanide concentration after acidification and distillation of the medium to release the cyanide, which was then trapped in NaOH and run through a dionex. In the case of the iron cyanides, over 95% of the cyanide was removed from the medium containing the fungus, whereas over 90% of the original cyanide concentration remained in the control medium.

The dominant fungal species has been identified as a Fusarium sp. Another fungal species Trichodermata sp has also been identified along with Fusarium sp and Penicillium sp.

Material (1 g) from either a spent oxide heap or contaminated soil from the edge of the site was added to the medium and left to shake (aerate) at 25° C. in the dark. These enrichment samples had been taken from a disused gasworks site about six weeks earlier and stored at 4° C.

After 10 days the flasks were allowed to settle and 5 ml of medium was transferred into 100 ml of fresh pH4 medium again containing 0.25 mM $(Ni(CN)^{2-}$ as the sole nitrogen source. This procedure was repeated after 7 days but this time medium containing no nitrogen source was also inoculated.

Growth of a fungus (or fungi) became evident as a black mat in flasks containing a fungal inoculum or originally from the enrichment flask containing the contaminated soil. No growth of micro-organisms was evident from the enrichment flasks which contained only the spent oxide. No growth was visible in the flasks with no added nitrogen.

Two more consecutive sub-cultures were carried out, again into medium containing either no nitrogen source, or 0.5 mM $Ni(CN)_4^{2-}$ as the sole nitrogen source. Again growth was only visible with the $Ni(CN)_4^{2-}$. Growth was also found with 0.5 mM $Cu(CN)_4^{2-}$ or with ammonia as the source of nitrogen; however with ammonia although fungal growth was visible, the medium became cloudy suggesting bacterial growth was also occurring.

Following the enrichment process, medium was set up with 0.5 mM of either $K_4Fe(CN)_6$ or $K_3Fe(CN)_6$ added as the sole nitrogen source. When either salt is added to the medium it dissolves completely to release $K^+$ and either $Fe(CN)_6^{4-}$ or $Fe(CN)_6^{3-}$ ions respectively. The $Fe(CN)_6$ ions do not dissociate due to their stability, however on addition of the trace elements, which contain free iron, the $Fe(CN)_6$ ions react immediately with the trace amounts of iron to precipitate Prussian Blue ($Fe_4[Fe(CN)_6]_3$); H. Meeussen, personal communication). Initially the colour of the medium with added $K_4Fe(CN)_6$ is blue, whereas with $K_3Fe(CN)_6$ the medium is green; this difference is probably due to the different amounts of potassium co-precipitated with the Prussian Blue, however over time and exposure to light, both media become bright blue as further Prussian Blue forms when the $Fe(CN)_6$ ions start to slowly decompose to release small amounts of $CN_-$ and free ion (H. Meeussen, personal communication). The free iron then immediately reacts with the rest of the $Fe(CN)_6$ to form Prussian Blue. This latter reaction also occurs if trace elements without the iron are added to the medium.

In precipitated Prussian Blue, part of the iron is present as $Fe^{2+}$ and part as $Fe^{3+}$. In order to form Prussian Blue it is necessary that the medium contains either $Fe^{2+}$ and $Fe(CN)_6^{3-}$ or $Fe^{3+}$ and $Fe(CN)_6^{4-}$. Both combinations result in a similar precipitate of Prussian Blue. If both forms are in the oxidised form ($Fe^{3+}+Fe(CN)_6^{3-}$) or the reduced form ($Fe^{2+}+Fe(CN)_6^{4-}$) Prussian Blue will tend not to form, however the oxidised form is highly oxidising and will react with organic material, for example, succinate buffer present in the microbial pH4 growth medium, to form the necessary reduced forms to precipitate Prussian Blue. Likewise the reduced combination is also very reactive and will react with the air to partly oxidise and again precipitate as Prussian Blue.

Approximately 20 days after the fungus (5% inoculum) was added to the iron cyanide medium (where either $K_4Fe(CN)_6$ or $K_3Fe(CN)_6$ had been added) growth was visible as a black mat and the media became colourless.

A control experiment was set up with flasks containing either $K_4Fe(CN)_6$, $K_3Fe(CN)_6$ (both of which react to produce Prussian Blue, as detailed above), $Ni(CN)_4^{2-}$, or no nitrogen source. In each case the medium was inoculated with 5% of fungus from medium containing the respective nitrogen source; the no nitrogen control was inoculated from the previous $Ni(CN)_4^{2-}$ growth medium. Control flasks which were uninoculated were also set up. The flasks were placed in a dark shaking incubator at 25° C. to aerate, however they were take into the light periodically for observation.

In all cases growth was visible in flasks containing a nitrogen source. No growth was visible in the no nitrogen control. In flasks which contained an iron cyanide (giving Prussian Blue) and the fungus, the medium (at about pH4) became colourless after approximately 20 days, however with the uninoculated flasks the medium remained bright blue. When allowed to stand in the light a blue precipitate of Prussian Blue was also visible in the $K_4Fe(CN)_6$ or $K_3Fe(CN)_6$ control flasks.

Disappearance of cyanide in the inoculated flasks was also measured by acidification and distillation of the medium to release to cyanide from any complex. The free cyanide was trapped in NaOH which was analysed using a Dionex system. In the case of the iron cyanides, over 95% of the cyanide in the medium containing the fungus was degraded, whereas over 90% of the original cyanide concentration remained in the control (uninoculated) medium. With the $Ni(CN)_4^{2-}$ although no cyanide was recovered from the inoculated flask, very little cyanide was recovered from the control flask due to the instability of this complex at pH4. This analysis is shown in FIG. 1.

The pH values of the inoculated medium and the control flasks were also measured after 26 days. In all cases where growth occurred there was an increase in the pH (see FIG. 2).

What is claimed is:

1. A method for biodegrading at least one iron cyanide complex, comprising causing a fungus selected from *Fusarium solani* (CABI 380003), *Trichoderma polysporum* (CABI 380004), *Penicillium miczynski* (CABI 380005), *Fusarium oxysporum* (CABI 380006), and *Scytalidium thermophilum* (CABI 380007) to grow in a medium containing the cyanide complex, wherein the pH of the medium is 7.5 or less.

2. The method of claim 1, in which a mixture of two or more iron cyanide complexes is biodegraded.

3. The method of claim 1, wherein the pH of the medium is 6 or less.

4. The method of claim 3, wherein the pH of the medium is between 3 and 6.

5. The method of claim 1, wherein the iron cyanide complex comprises Prussian Blue.

* * * * *